US011307210B2

(12) United States Patent
Eberle

(10) Patent No.: US 11,307,210 B2
(45) Date of Patent: Apr. 19, 2022

(54) CONVEYING DEVICE

(71) Applicant: ANDREAS HETTICH GMBH & CO. KG, Tuttlingen (DE)

(72) Inventor: Klaus-Guenter Eberle, Tuttlingen (DE)

(73) Assignee: ANDREAS HETTICH GMBH & CO. KG, Tuttlingen (DE)

(*) Notice: Subject to any disclaimer, the term of this patent is extended or adjusted under 35 U.S.C. 154(b) by 201 days.

(21) Appl. No.: 16/086,589

(22) PCT Filed: Mar. 16, 2017

(86) PCT No.: PCT/EP2017/056305
§ 371 (c)(1),
(2) Date: Sep. 19, 2018

(87) PCT Pub. No.: WO2017/167585
PCT Pub. Date: Oct. 5, 2017

(65) Prior Publication Data
US 2019/0101552 A1 Apr. 4, 2019

(30) Foreign Application Priority Data
Mar. 29, 2016 (DE) .................... 10 2016 105 683.9

(51) Int. Cl.
*G01N 35/00* (2006.01)
*C12M 1/22* (2006.01)
(Continued)

(52) U.S. Cl.
CPC ....... *G01N 35/00029* (2013.01); *C12M 23/10* (2013.01); *C12M 23/50* (2013.01);
(Continued)

(58) Field of Classification Search
CPC ............................................... G01N 35/0029
See application file for complete search history.

(56) References Cited

U.S. PATENT DOCUMENTS 4,572,067 A 2/1986 Fischer
2005/0186114 A1* 8/2005 Reinhardt .......... G01N 35/0099
422/65
(Continued)

FOREIGN PATENT DOCUMENTS

CN 104973301 A 10/2015
DE 102010044125 A1 * 5/2012 ............ C12M 29/00
(Continued)

OTHER PUBLICATIONS

English translation of DE-102010044125-A1. (Year: 2012).*
(Continued)

*Primary Examiner* — Matthew D Krcha
(74) *Attorney, Agent, or Firm* — Woodling, Krost and Rust

(57) ABSTRACT

The invention relates to a conveying device (IO) for positioning and providing laboratory vessels (12; 12*a*, 12*b*, 12*c*) for nutrient media, samples, microorganisms, cell cultures, or the like for analysis, sample preparation, and/or sample manipulation at an associated apparatus (64), comprising at least one first conveying unit (32) for conveying the laboratory vessels (12) between an initial region (30) and a provision region (60), where the laboratory vessel (12) is held for the analysis or preparation. According to the invention, a plurality of conveying units is present, which perform only a translational motion of the laboratory vessel (12) along an axis, wherein the first conveying unit (32) vertically conveys the laboratory vessel (12) from the initial region (30) to a predetermined height region (50) and vice versa, and a second conveying unit (56) is provided, which horizontally conveys the laboratory vessel (12) from the height region (50) to the provision region and vice versa.

14 Claims, 3 Drawing Sheets

(51) Int. Cl.
  *C12M 1/00* (2006.01)
  *C12M 3/00* (2006.01)
  *C12M 1/26* (2006.01)
  *C12M 1/36* (2006.01)
  *G01N 35/04* (2006.01)

(52) U.S. Cl.
  CPC ....... *G01N 35/00732* (2013.01); *C12M 23/48* (2013.01); *C12M 33/00* (2013.01); *C12M 41/48* (2013.01); *G01N 2035/00039* (2013.01); *G01N 2035/0093* (2013.01); *G01N 2035/0427* (2013.01); *G01N 2035/0441* (2013.01); *G01N 2035/0455* (2013.01); *G01N 2035/0465* (2013.01)

(56) References Cited

U.S. PATENT DOCUMENTS

| | | |
|---|---|---|
| 2008/0063562 A1 | 3/2008 | Hoover et al. |
| 2010/0101339 A1* | 4/2010 | Tatsutani ............... G16H 10/40 73/863.91 |
| 2010/0172735 A1* | 7/2010 | Gupta .................... C12M 23/10 414/768 |
| 2011/0243814 A1 | 10/2011 | Brelivet |
| 2012/0277905 A1 | 11/2012 | Botma et al. |
| 2013/0083330 A1* | 4/2013 | Piana ........................ G01V 8/20 356/614 |
| 2013/0183132 A1 | 7/2013 | Gupta et al. |
| 2014/0030802 A1* | 1/2014 | Eberle ..................... C12M 45/22 435/303.1 |
| 2014/0234978 A1 | 8/2014 | Heise et al. |
| 2015/0198622 A1 | 7/2015 | Botma et al. |
| 2016/0054344 A1 | 2/2016 | Heise et al. |
| 2016/0083686 A1 | 3/2016 | Triva |
| 2017/0097372 A1 | 4/2017 | Heise et al. |
| 2018/0074087 A1 | 3/2018 | Heise et al. |

FOREIGN PATENT DOCUMENTS

| | | |
|---|---|---|
| DE | 102010044125 A1 | 5/2012 |
| DE | 102010060634 A1 | 5/2012 |
| JP | H06225753 | 8/1994 |
| WO | 2008083440 | 7/2008 |

OTHER PUBLICATIONS

German Patent and Trademark Office, German Search Report, dated Nov. 9, 2016, pp. 1-12, Application No. 102016105683.9, Applicant: Andreas Hettich GmbH & Co. KG.

European Patent Office, International Search Report, dated Jul. 4, 2017, pp. 1-6, Application No. PCT/EP2017/056305; Applicant: Andreas Hettich GmbH & Co. KG.

European Patent Office, Written Opinion of the International Search Report, pp. 1-7, Application No. PCT/EP2017/056305, Applicant: Andreas Hettich GmbH & Co. KG.

The State Intellectual Property Office of China, Office Action, dated Aug. 24, 2021, pp. 1-5, Application No. 201780020961.0.

The State Intellectual Property Office of China, Translation of Office Action, dated Aug. 24, 2021, pp. 1-11, Application No. 201780020961.0.

* cited by examiner

CONVEYING DEVICE

PCT/EP2017/056305, international application filing date Mar. 16, 2017 claims the benefit and priority of and to German patent application no. 10 2016 105 683.9, filed Mar. 29, 2016.

PCT/EP2017/056305 and German patent application no. 10 2016 105 683.9 are incorporated herein by reference hereto in their entireties.

The invention relates to a conveying device for positioning and providing laboratory vessels for samples, microorganisms, cell cultures or the like for analysis, sample preparation and/or sample manipulation on an associated device.

In the prior art, conveying units in devices for analyzing or processing biological material are known which use grippers that individually pick up laboratory vessels, usually petri dishes arranged in stacks, in an input area and convey them to an analysis area. During analysis, the gripper holds the petri dish and then, depending on the setup of the device, either returns it to the input area or forwards it to a dedicated output area.

For this purpose, actuators move a single gripper along a plurality of axes, both linearly and rotationally. This can easily be implemented in terms of design and at relatively low costs.

The higher the number of axes along which the gripper is moved, however, the lower will be the degree of positioning accuracy. But deviations of merely a few millimeters from the position into which a petri dish has to be brought for analysis will already lead to inaccurate results A generic conveying device is known from US 2016/0083686 A1. This conveying device comprises at least a first conveying unit for feeding and/or removing laboratory vessels from an initial region to a provision region where the laboratory vessel is retained for analysis or preparation. In this case, a plurality of conveying units are provided, each of which perform only a translational movement of the laboratory vessel along one axis. The first conveying unit vertically conveys the laboratory vessel from the initial region to a predetermined height region and vice versa. A second conveying unit is provided which horizontally conveys the laboratory vessel from the height region to the provision region and vice versa. However, the alignment to the analysis device is not accurate enough in this case.

It is the object of the invention to further develop a conveying device for positioning and providing laboratory vessels so as to ensure the accurate positioning of laboratory vessels in any number of runs, while avoiding the above mentioned disadvantages.

The invention is based on the finding that a plurality of serially arranged actuators which each perform a single movement along an axis, can be used instead of a multi-axis actuator which performs the complete movement. This allows the laboratory vessel to be positioned and retained more accurately with respect to the analysis device. Moreover, it is possible to interpose additional measures for verifying and improving its orientation and arrangement. This increases the flexibility and accuracy of the system.

According to the inventive embodiment, a plurality of conveying units are present which merely perform a translational movement of the laboratory vessel along an axis, with a first conveying unit being provided which vertically conveys the laboratory vessel, in particular a petri dish, from an initial region to a predetermined height region and vice versa, and a second conveying unit which horizontally conveys the petri dish from the height region to the provision region and vice versa. Because the vertical conveyance and the horizontal conveyance are assigned to different actuators, the positioning accuracy of the laboratory vessel can be significantly increased. Consequently, much more accurate and reliable results can be expected in the subsequent analysis or preparation because the laboratory vessel is exactly aligned to the device.

In addition, a centering device is provided which centers the laboratory vessel relative to the axis of the first conveying unit. Therefore, the laboratory vessel has already been pre-centered at the time it is transferred from the first conveying unit to the second conveying unit, and the second conveying unit need only make small corrections, if necessary, in the positioning of the laboratory vessel, for the laboratory vessel to be retained precisely in the position required for its analysis in the provision region. This further improves the performance of the conveying device.

In this case, the first conveying unit has a support for the laboratory vessel, which support is oriented horizontally, and the axis of the first conveying unit extends vertically thereto. The third conveying unit moves the laboratory vessel horizontally far enough for the latter to then rest on a support of the first conveying unit in the initial region. A movement of the first conveying unit then causes the laboratory vessel resting on the support to reach the predetermined height region where it is taken over by the second conveying unit. This solution is simple and inexpensive.

In addition, the centering device comprises a rotational drive for the support and a lateral ring guide for the laboratory vessel which conically decreases in one direction. For centering the laboratory vessel, the support moves together with the laboratory vessel in the direction in which the conical ring guide decreases. The inner diameter of the ring guide is dimensioned such that it is larger at its maximum extension than the diameter of the largest laboratory vessel to be used. At its smallest extension, the inner diameter of the ring guide is smaller than the diameter of the smallest laboratory vessel to be used, so that the laboratory vessel is supported on the ring guide at the end of the centering process. Rotation of the support during movement in the direction in which the conical ring guide decreases in size thus counteracts tilting and in particular a tilt of the laboratory vessel in the ring guide. This is a simple way of achieving a fast and reliable centering, and thus an accurate alignment, of the laboratory vessel relative to the device used for the analysis or preparation.

In an advantageous embodiment of the invention, a third conveying unit is provided which horizontally conveys a laboratory vessel from an input region to the initial region. This allows the input region to be arranged at a greater distance from the initial region, for example, which allows for greater flexibility in the input of laboratory vessels.

It is considered advantageous to additionally provide a fourth conveying unit which horizontally conveys a laboratory vessel from the initial region to the output region. By providing an output region which is remote from the input region, higher load capacities of laboratory vessels can be achieved. Furthermore, this in principle allows continuous conveying and analysis since the input of laboratory vessels into the conveying device and the output of the laboratory vessels from the conveying device are independent of each other. The performance of the conveying device is thus more efficient.

Preferably, the support can be moved up and down along the vertically aligned axis. An upward and downward movement along a vertically aligned axis is easy to implement and less prone to failure.

In particular the rotational drive is an integral part of the first conveying unit.

In another advantageous embodiment, the direction in which the laboratory vessel is introduced into the ring guide, and the direction of travel into the provision position are opposite to each other. The laboratory vessel therefore only has to be moved along one axis for centering and for moving it into the provision position. This simplifies the construction of the conveyor, reduces the potential for errors and reduces costs.

Preferably, the rotational axis of the centering device and the vertical axis of the first conveying unit are identical. This makes it easier to integrate the support, the rotational drive and the axis of the first conveying unit with each other. As a result, the construction of the first conveying unit and the centering device becomes simpler, less error-prone and less expensive.

In particular to prevent misaligned laboratory vessels from being conveyed into the analysis area, at least one position sensor is arranged upstream of the initial region, which sensor detects the alignment of the laboratory vessel with respect to top and bottom. This saves time during the transport process because laboratory vessels can be conveyed directly to the output region once their misalignment has been detected. If the alignment of the laboratory vessels to be conveyed is irrelevant for the purposes of analysis/preparation/manipulation, then the position sensors can simply be deactivated or omitted.

In a further aspect of the invention, the laboratory vessel is of a rotationally symmetrical design and has different diameters over its height. In particular, the laboratory vessel has a container which is open towards the top and which has a first outer diameter, and a lid to close the container which lid has a second outer diameter, with said second outer diameter being larger than said first outer diameter. The different outer diameters make it easier to distinguish the container from the lid. The rotationally symmetrical design facilitates the overall handling of the laboratory vessel because during input, gripping and output, the alignment of the laboratory vessel with regard to the horizontal plane can be neglected. This makes the conveying device more efficient and safer. Also conceivable are vials and/or cylindrical vessels filled with liquid.

It is advantageous for a position sensor module to be mounted in the conveying path of the third conveying unit. If the position sensor detects a misaligned laboratory vessel, then the third conveying unit can convey such laboratory vessel directly to the output area without first activating the centering device and/or the first conveying unit. This saves time and improves the operation of the conveying device.

It is expedient to provide two light barriers which are aligned transversely to the conveying direction of the third conveying unit and which are each associated with an outer diameter of the laboratory vessel so that the light barrier first generates a signal at which the larger outer diameter of the laboratory vessel enters first, and then, with some delay, the other light barrier at which the smaller outer diameter enters, which allows the alignment of the laboratory vessel to be determined. This type of determination is reliable and inexpensive, its advantages are, among others, a non-contact measurement and good electromagnetic compatibility.

As it is common practice in the laboratory to bar-code laboratory vessels such as petri dishes for their unambiguous identification, at least one bar code scanner is provided in one embodiment of the invention. To be able to read bar codes of various different standard formats both on the side and on the bottom of the laboratory vessels, it is expedient to use two bar code scanners which are arranged according to the bar codes. The bar code is used to clearly identify the laboratory vessels and thus also the samples and their properties.

Preferably, the bar-code reading process is combined with a rotary movement of about 360° of the first conveying unit. This movement makes it possible to read bar codes regardless of the horizontal orientation of the laboratory vessels.

After the bar code has been read successfully, it is expedient to continue the rotary movement additionally by a defined angle in order to bring the lateral bar code into a defined horizontal position. This orientation can prevent the bar code from possibly being damaged by the gripper of the second conveying unit.

In a preferred embodiment, the second conveying unit is formed by a transport arm having a gripper at its free end. Transport arms can be advantageously used for conveying laboratory vessels also over longer distances. Grippers are well suited for picking up and transporting laboratory vessels, in particular petri dishes, and can easily be adapted to the different dimensions of the laboratory vessels. The combination of transport arm and gripper makes for a wider range of applications of the second conveying unit and thus of the conveying device.

Preferably, the gripper is rotatably mounted and driven in the transport arm, thus enabling it to rotate, in particular by 180°, the gripped part of the laboratory vessel into a predetermined orientation relative to the analysis device and to move it horizontally. For example, it is common practice to store petri dishes such that the container is at the top and the lid at the bottom. The open side of the container thus faces down, amongst other to prevent moisture from condensing on the nutrient medium. Analyzers in turn are frequently designed such that a detection unit, such as a camera, is directed from above on the samples to be analyzed. The laboratory vessel thus frequently needs to be rotated by 180° for an analysis to be performed on it. In such a case, the rotatable design of the gripper enables such a rotation and thus increases the range of use of the conveying device.

In an advantageous development of the invention, a suction device including a HEPA filter is provided which is effective at least between the height region and the provision region. Above all, this suction device is effective when the lid is separated from the dish and in the area of rotation since dangerous particles may be released during these processes. Dangerous, pathogenic or toxic substances can thus be prevented from being released into the environment during the analysis. This makes the conveying device clearly safer in use.

Furthermore, it is very advantageous if a sensor is provided which detects when the laboratory vessel vertically moved by the first conveying unit has reached a predetermined height level. This data can then be used to control the first conveying unit so that the laboratory vessel is conveyed to the predetermined height level depending on its overall height and is thus held at precisely the required distance from the analyzing unit. Laboratory vessels of different sizes can therefore be correctly positioned by the second conveying unit. This improves the range of use of the conveying device.

According to yet another aspect of the invention, the object of the method according to the present invention is accomplished by the use of a conveying device for the positioning and providing laboratory vessels for samples, microorganisms, cell cultures or the like for analysis on an associated analysis device, in particular of the above mentioned type, wherein the orientation of the laboratory vessel is first detected before the laboratory vessel is conveyed to the initial region by the first conveying unit. This is necessary if the orientation of the laboratory vessel is relevant for the subsequent steps. If the orientation conforms to the predetermined orientation, the laboratory vessel is centered in the initial region. However, if the orientation of the laboratory vessel does not correspond to the predetermined orientation, the laboratory vessel is removed from the initial region again, in particular by means of the third conveying unit.

This ensures that only laboratory vessels that are properly aligned and can thus be analyzed, prepared or manipulated by the device will be conveyed to the analyzer by the first conveying unit. This saves time and reduces the number of non-usable results. The efficiency of the analysis of samples is increased by the proposed conveying device.

According to one aspect of the invention, the laboratory vessel is centered relative to the vertical axis before being moved to the height region. In the height region, the second conveying unit can thus already take over the laboratory vessel in a predetermined position to which the second conveying unit only needs to make some fine adjustment in order to precisely position the laboratory vessel within the analysis device as is required for an optimum analysis. This prevents inaccuracies in the analysis due to poor positioning of the laboratory vessel and further increases the expected reliability of the analysis result.

Preferably, the laboratory vessel is opened before the analysis and closed again after the analysis.

In normal operation, it is expedient for the laboratory vessels to be moved from the input region to the initial region by the third conveying unit, for the laboratory vessels to be moved from the initial region to the height area and vice versa by the first conveying unit, and for the laboratory vessels to be moved to the provision area by the second conveying unit. The third conveying unit moves the laboratory vessel from the initial position on to the beginning of the conveyor belts of the fourth conveying unit. The conveyor belts of the fourth conveying unit are used to transport the laboratory vessel to the desired position in the output region. On the one hand, this allows maximum precision to be achieved when positioning the laboratory vessels since the individual conveying units only perform translational movements along one axis at a time. On the other hand, the movements of the conveying units can easily be synchronized, which saves time in each conveying cycle. The conveying of the laboratory vessels thus becomes both safer and more efficient.

According to a preferred method, a control unit which cooperates with the position sensor makes sure that only laboratory vessels that are aligned in a predetermined way remain in the initial region, for being moved into the provision position, and all others are conveyed out of the initial region again, in particular by the third conveying unit. This ensures that only correctly aligned laboratory vessels which can thus be analyzed by the analysis device will be conveyed to the analysis device. This saves time, and reduces the number of results that cannot be used. The use of the proposed conveying device increases the efficiency of the conveyance and of the analysis of samples.

It is advantageous if at least the part of the laboratory vessel which is relevant for the analysis or which is to be prepared is gripped from the height area by the second conveying unit, and that this part of the laboratory vessel is returned to the provision position, is retained during analysis and returned to the provision position after the analysis. This eliminates the need to remove the lid from the container in a separate step from the conveyance, and to store it intermediately, if necessary. This makes the conveyance faster and more efficient, whilst at the same time reducing the danger of losing a lid.

In addition, it is very advantageous if the laboratory vessel is introduced into the centering device as the support rotates together with the laboratory vessel. This rotational movement acts to center the laboratory vessel slowly and uniformly which prevents the laboratory vessel from being tilted and canted, at worst. This improves the safety of the centering and conveyance processes.

Further advantages, features and possible applications of the present invention will become apparent from the following description in which reference is made to the embodiments illustrated in the drawings.

Throughout the description, the claims and the drawings, those terms and reference characters are used as are listed in the enclosed List of Reference Characters. In the drawings:

Figure 1:
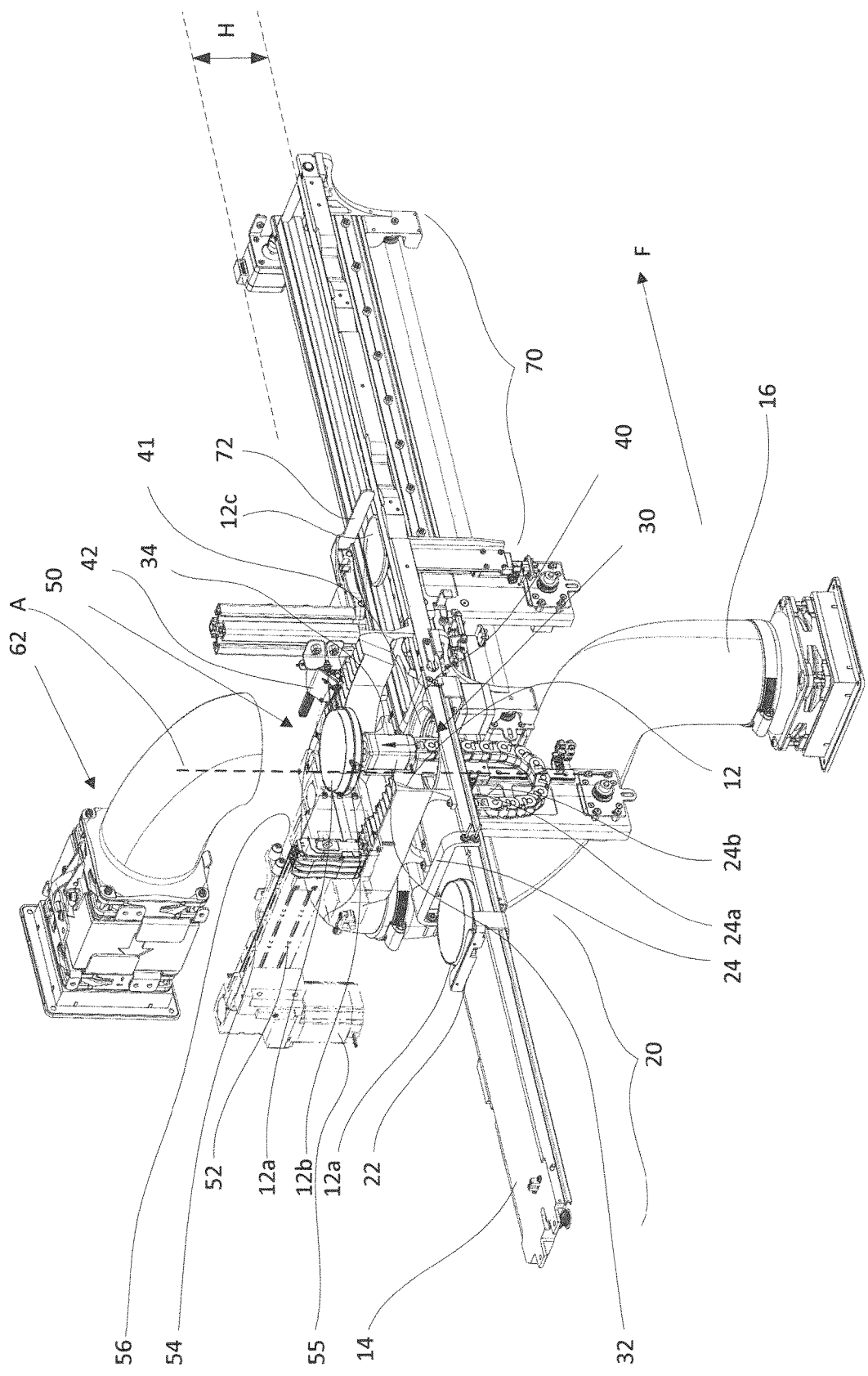
FIG. 1 is a perspective view of a conveying device according to the invention.

FIG. 1 is a perspective view of a conveying device 10 according to the invention without mountings, connections to a housing or interfaces to other modules/components of a possible overall system. In the conveying device 10, laboratory vessels, in particular petri dishes 12, are conveyed on a conveyor track 14.

Provided below the conveyor track 14 is an S-shaped suction unit 16 with a filter so as to immediately remove any germs, bacteria and the like as may be released when the petri dishes are opened, thus at any rate preventing contamination of the environment and of the conveying device 10. The suction device 16 sucks in ambient air which is then filtered and discharged in the direction of the petri dish 12. Opposite the upper end of the suction unit 16 a suction device 62 is provided which sucks in the air discharged by the suction unit 16, which air flows around the petri dish 12 and thus forms a flow wall that prevents any leakage of germs. A HEPA filter is arranged in the suction device 62 which filters the air of germs. The filtered air is then discharged to the environment again from the suction device 62. The air flow thus passes from the bottom to the top.

The petri dishes 12 are of the conventional two-part design, and comprise a container 12*a* and a lid 12*b* which encloses the container in certain areas and closes the container. As seen from the left, the conveyor track 14 has an input region 20 via which the petri dishes 12 are introduced manually or automatically into the conveying device 10. A pusher 22 moves the petri dish 12 into an initial region 30 of the conveyor track 14 adjacent to the input region 20 of the conveyor track 14, as seen from the right, which initial region 30 will be explained in more detail later.

The initial region 30 in turn is followed by an output region 70 of another conveyor track 15 in which the petri dishes 12 are removed from the conveying device 10 manually or automatically. A barrier 72 is provided in the output region 70, which barrier prevents the petri dishes 12 from being conveyed too far. The petri dishes 12 are stopped by the barrier 72. A conveyor belt of the additional conveyor track 15 transports the petri dishes 12 from the initial region 30 to a location of the output region 70 which is remote from the initial region 30.

This arrangement results in a global conveying direction F in which the pusher 22 and the conveyor belt of the conveyor track 15 move together with a petri dish 12.

The pusher 22 extends over the conveyor track 14 in the manner of a bracket on one side and is driven in or against the conveying direction F in a conventional manner by an electric motor mounted below the conveyor 14. In this arrangement, the pusher 22 is exclusively assigned to the conveyor track 14.

The additional conveyor track 15 comprises a conveyor belt that consists of two belts. The conveyor belt is not of the continuous type so as to enable a subsequent sorting unit (not shown here) to also transport the petri dish 12 vertically upwards.

FIG. 1 shows the pusher 22 together with a petri dish in the input region 20. Provided on the conveyor track 14, between the input region 20 and the initial region 30, is a position sensor module 24 which is connected to a central control unit not shown here. This position sensor module 24 comprises two light barriers 24a and 24b which are arranged vertically the one above the other and which are spaced from each other in such a way that the upper light barrier 24a detects the top part 12a or 12b of the petri dish 12 which passes the position sensor module 24 and the lower light barrier 24b detects the bottom part 12b or 12a of the petri dish 12.

The different diameters of the container 12a and of the lid 12b of the petri dish 12 make it possible for the position sensor 24 to detect the orientation of the petri dish 12. The lid 12b of the petri dish 12 surrounds the container 12a in certain areas and thus has a larger diameter than the container 12a. As a result, the first one of the two light barriers 24a and 24b, which is interrupted first, detects the passage of the lid 12b and the second one detects the passage of the container 12a.

For the embodiment of the invention described here it is required that the petri dishes 12 are inserted with the lid 12b at the bottom and the container 12a at the top. Firstly, petri dishes 12 are frequently stored in this orientation. Secondly, this orientation of the petri dishes 12 is advantageous for the processing of samples, since the container 12a can easily be removed and replaced after processing, which eliminates the additional step of removing the lid 12b, storing it temporarily during processing and subsequently putting it back on.

Figure 2:
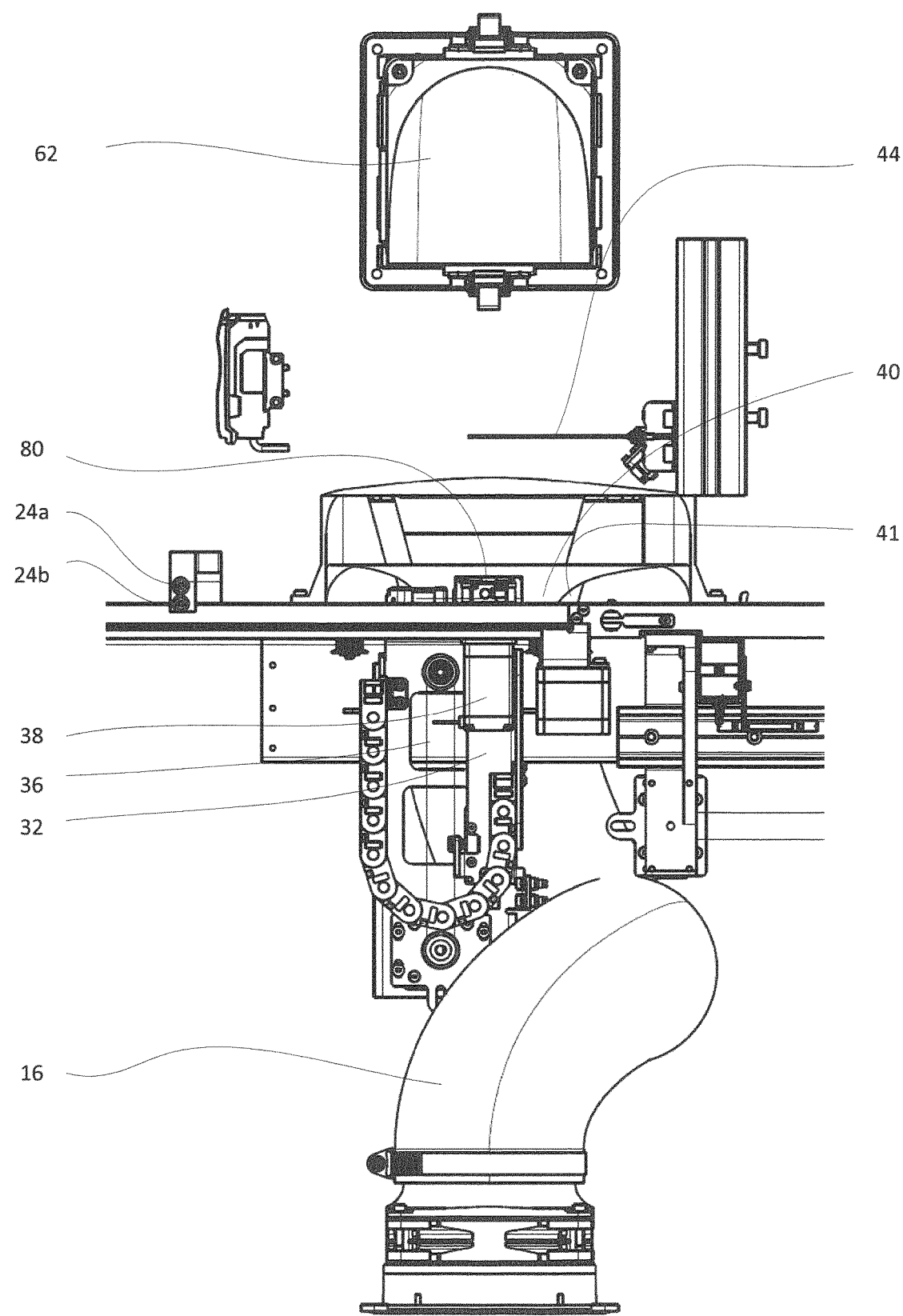
FIG. 2 is a lateral sectional view of a central portion of the conveying device which comprises an initial region and a height region.

In the initial region 30, the conveyor track 14 has a circular recess 40 with a conically tapered lateral ring guide 41, see FIG. 2. A lifting device 32 which is vertically movable along an axis A reaches through the recess 40. The lifting device 32 comprises a drive 36 for the vertical displacement and a support plate 34 which can be rotated about axis A. The diameter of the support plate 34 is dimensioned such that it can pass with minimal clearance through the recess 40 of the conveyor track 14 at the point of its smallest diameter. Mounted below the support plate 34 is an electrical drive 38 for rotational movement of the support plate 34.

The support plate 34 which can be vertically displaced and rotated together with the lifting device 32 and the recess 40 with its conically tapered lateral ring guide 41 together form a centering device for the exact centering of the petri dishes 12. The centering process will be discussed in more detail.

FIG. 1 shows a petri dish 12 which is precisely centered on the support plate 34, with the support plate 34 together with the petri dish 12 being located above the conveyor track 14 in a height region 50.

On a level with the height range 50 there is a provision area for the subsequent analysis/manipulation/preparation of samples by a device not shown here, for example an analyzer for the samples contained in the petri dish container 12a.

The petri dish 12, more specifically the container 12a resting on the lid 12b, is picked up by a gripper 52 in the height region 50, subsequently the support plate 34 is moved downward by at least the radius and the height of the lid plus a safety distance, in particular all the way down. The gripper 56 now only carries the container 12a. The gripper 56 rotates the container 12b by 180° and translationally moves it into a provision area. In the provision region, the sample contained in the container 12a is then analyzed by an analyzer not shown here. The petri dishes 12 or containers 12a of the petri dish 12 are arranged in the provision region in the separate analysis or preparation unit.

The gripping device 52 comprises a support arm 54, and mounted on the free end of the support arm 54 is the gripper 56. A drive 55 is provided which can be used to move the support arm 54 forward and back orthogonally relative to the conveying direction F. The gripper 56 is provided with a drive 58 which is used to rotate it about the longitudinal axis of the support arm 54. The translational movement of the support arm 54 is used to translationally convey petri dish containers 12a between the height region 50 and an analyzing unit. Furthermore, the orientation of a gripped petri dish 12 and/or a part of a petri dish 12 can be changed with regard to top and bottom by a rotational movement of the gripper 56. This will be explained in more detail below in connection with the method.

As shown in FIG. 1, another petri dish 12c is located in the output region 70. In accordance with the conveying direction F, the petri dish 12c, having already passed the analysis process, is ready for withdrawal from the output region 70.

Figure 3:
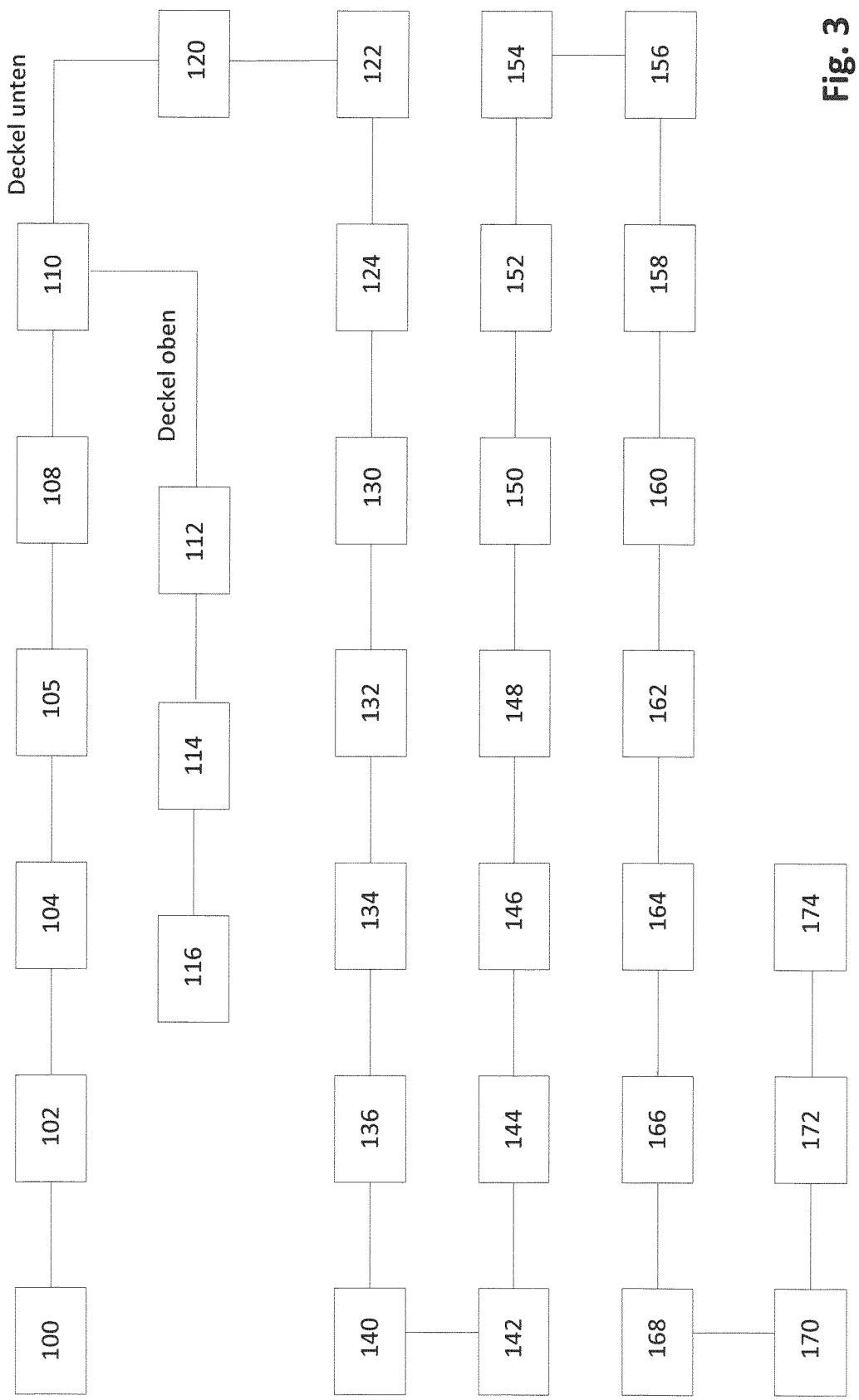
FIG. 3 is a flow chart which illustrates a possible flow of a method.

FIG. 3 is a flowchart illustrating a possible flow of a method. This more clearly illustrates the interaction of the previously described elements of the conveying device 10.

Once a petri dish 12 has been introduced 100 into the input region 20 of the conveying device 10, the pusher 22 conveys 102 the petri dish 12 along the conveyor track 14 toward the initial region 30. Between the input region 20 and the initial region 30, the petri dish 12 passes 104 the position sensor 24 which is connected to the control unit. Because the outer diameter of the lid 12b of the petri dish 12 is larger than that of the container 13a, the one of the two vertically stacked light barriers 24a and 24b of the position sensor 24 which is assigned to the plane of the lid 12b will be the first to generate 106 a signal.

The signal generated 106 first is evaluated 110 by the control unit. At the same time, the lifting device 32 is moved vertically by the drive 36 to such an extent that the support plate 34 and the conveyor track 14 are in one plane. In accordance with the method of the invention, it is necessary for the petri dish 12 to be inserted with the lid 12b at the bottom and the container 12a at the top. If the evaluation 110 by the control unit shows that the signal first generated 106 comes from the light barrier 24a and consequently the lid 13b is arranged at the top, processing of the petri dish 12 is terminated 112. The pusher 22 moves 114 together with the petri dish 12 via the initial region 30 across to the conveyor belt of the additional conveyor track 15, then the conveyor belt takes over the transport to the output region 70. Then the pusher 22 moves 116 back to the input region and is ready to convey 102 another petri dish 12.

If the evaluation 108 by the control unit shows that the signal generated 106 first comes from the light barrier 24*b* and consequently the lid 12*b* is arranged at the bottom, the pusher 22, along with the petri dish 12, moves 120 back to the initial region 30 until the petri dish 12 rests 122 on the support plate 34. The pusher 22 then moves 124 back into the input region 20 and is ready to convey 102 another petri dish 12.

For the precise centering of the petri dish 12, the support plate 34 together with the petri dish 12 is made to rotate 130 by the drive 38. At the same time, the lifting device 32 begins to move 132 downward. During this downward movement along the downward conically tapered ring guide 41 of the recess 40 made in the initial region 30, the petri dish 12 resting on the support plate 34 is centered until it ultimately rests 134 completely on the ring guide 41.

The lifting device 32 continues to move 136 downward until the support plate 34 is located completely below the ring guide 41. This ensures that the petri dish 12 is centered on the ring guide 41.

The barcode scanner 44 reads 140 the barcode on the laboratory vessel 12 and the evaluation unit 46 evaluates 142 the barcode. This process 140 of reading the barcode is performed before the petri dishes 12 are lifted. The barcode is either located at the bottom of the petri dish 12, as in this case, at the top—as viewed from the top, because the dishes are inverted, or on the side of the petri dish 12. To be able to detect barcodes at the bottom and on the side alike, two barcodes are required. In the case of a lateral barcode, the petri dish 12 is rotated by a maximum of 180° by the rotation device 38 until the barcode scanner 80 mounted on the side has detected the barcode. Once the barcode has been detected, the rotational movement is continued by a defined angle in order to align the side barcode to the front and thus to prevent the tips of the gripper 56 from damaging the barcode.

Next, the lifting device 32 moves upward 144 again and picks up 146 the petri dish 12. Together with the petri dish 12 resting on the support plate 34, the lifting device 32 continues its movement 148 until the height sensor 42 detects 150 the petri dish 12 at a predetermined height in the height region 50, sends 152 a signal to the central control unit and the central control unit then controls 154 the lifting device 32 so as to stop the travel motion.

Subsequently, the central control unit controls 156 the gripping device 52 to cause it to grasp the petri dish container 12*a* and then to move the lifting device 32 downward 158 by a predetermined value. Subsequently, the drive 55 of the gripping device 52 is activated 160 in order to move the container 12*a* from the height region 50 into the provision region of the analysis or preparation unit.

As the support arm 54 is moved together with the container 12*a* into the provision region of the analysis or preparation region, the drive rotates 162 the gripper 56 together with the container 12*a* by 180° to cause the open side of the container 12*a* to face upward. The gripper 56 is closed by spring force without external influence so as to reliably hold the petri dish container 12*a* during the analysis or preparation process without requiring a motor drive. It is opened by means of another motor.

Once the analysis 164 is completed, the support arm 54 together with the container 13*a* moves back from the analysis or preparation unit 64 into the height region 50, and at the same time, the drive rotates 166 the gripper 56 together with the container 12*a* by another 180° to its original orientation.

Once the gripper 56 has been moved into the height region 50, the lifting device 32, together with the lid 12*b*, moves to below the container 12*a*, and the gripper 56 releases 170 the container 12*a* onto the lid 12*b* resting on the support plate 34. The lifting device 32 now moves downward 172 together with the laboratory vessel 12 until the support plate 34 is flush with the conveyor track 14.

As a last step, the conveyor belts of the conveyor track 15 convey 174 the laboratory vessel 12 to the output region 70, where it can then be removed 172 manually or automatically.

LIST OF REFERENCE CHARACTERS 10 conveying device
12 petri dish
12*a* container
12*b* lid
14 conveyor track
15 additional conveyor track
16 suction unit
20 input region
22 pusher
24 position sensor
24*a,b* light barriers
30 initial region
32 lifting device
34 support plate
36 vertical drive
38 rotational drive
40 recess
41 ring guide
42 height sensor
44 barcode scanner
46 evaluation unit
50 height region
52 gripping device
54 support arm
55 drive (translational)
56 gripper
62 suction device
70 output region
72 barrier
80 lateral barcode scanner
100 a laboratory vessel 12 is introduced into input region 20
102 pusher 22 conveys laboratory vessel 12 toward initial region 30
104 laboratory vessel 12 passes position sensor 24
106 position sensor 24 sends signal to central control unit
108 lifting device 32 is moved by drive 36 until flush with conveyor track 14
110 control unit evaluates signal from position sensor 24
112 processing of laboratory vessel 12 is terminated
114 pusher 22 moves to output region 70 together with laboratory vessel
116 pusher 22 moves back to input region 20
120 pusher 22 conveys laboratory vessel 12 into initial region 30
122 laboratory vessel 12 rests on support plate 34
124 pusher 22 moves back to input region 20
130 drive 38 rotates support plate 34
132 lifting device 32 travels downward
134 laboratory vessel 12 rests on ring guide 41
136 lifting device 32 moves downward to below recess 40
140 barcode scanner 44 reads barcode on laboratory vessel 12
142 evaluation unit 46 evaluates barcode
144 lifting device 32 moves upward 146 support plate 32 receives laboratory vessel 12
148 support plate 32 moves upward together with laboratory vessel 12
150 height sensor 42 detects laboratory vessel 12
152 height sensor 42 sends signal to central control unit
154 central control unit controls lifting device 32 to stop
156 container part 12a of petri dish is grasped
158 lifting device 32 is moved downward by a predetermined value
160 container 12a is moved from height region 50 into provision region
162 drive rotates gripper 56 together with container 12a by 180°
164 support arm 54, together with container 12a, moves out of analysis unit 64
166 drive rotates gripper 56 together with container 12a by 180°
168 lifting device is moved to below container 12a
170 gripper 56 releases container 12a onto support plate 34
172 lifting device 32 moves downward together with petri dish 12 until support plate 34 is flush with conveyor track 14
174 conveyor belt of additional conveyor track 15 conveys laboratory vessel 12 into output region 70
A axis
H predetermined height
F conveying direction

The invention claimed is:

1. Conveying device (10) for positioning and providing laboratory vessels (12; 12a; 12b; 12c) for nutrient media, samples, microorganisms, cell cultures, for analysis, sample preparation, and/or sample manipulation on an associated apparatus (64), comprising:
    said conveying device includes a conveying direction F for said laboratory vessels;
    a first conveying unit (32) and a second conveying unit (52, 56, 54) operate independently with respect to each other, said first conveying unit (32) first translationally conveys said laboratory vessel (12) first between an initial region (30) and a predetermined height region (50) and then said second conveying unit (42, 56, 54) conveys said laboratory vessel (12) between said predetermined height region (50) and a provision region (64) and after said provision, said second conveying unit translationally conveys and returns said laboratory vessel (12) to said predetermined height region (50), and thereafter said first conveying unit (32) translationally conveys said laboratory vessel (12) back to said initial region (30);
    said first conveying unit (32) vertically and translationally conveys said laboratory vessel (12) from said initial region (30) to a predetermined height region (50) along a vertical axis (A) and vice versa;
    said first conveying unit (32) comprises a horizontally aligned support plate (34) for said laboratory vessel (12), said horizontally aligned support plate (34) includes a horizontally aligned support surface;
    said vertical axis (A) of said first conveying unit (32) extends orthogonally relative to said horizontally aligned support surface of said horizontally aligned support plate (34);
    said second conveying unit (52, 56, 54) comprises a support arm (54), said support arm (54) includes a longitudinal axis and a gripper (56) at a free end of said support arm;
    a drive (55) translationally moves said support arm (54) and said gripper (56) forward and backward orthogonally relative to said conveying direction F and said axis (A) in a horizontal plane;
    a drive (58) rotates said gripper (56) about said longitudinal axis of said support arm;
    said gripper of said second conveying unit (52) engages said laboratory vessel (12) and translationally and rotationally conveys said laboratory vessel (12) from said vertical axis (A) in said predetermined height region (50) to said provision region in said horizontal plane and vice versa;
    said laboratory vessel (12) is held in said provision region for analysis or preparation before it is returned to said predetermined height region (50) aligned with and along said vertical axis (A);
    a centering device (32, 40, 41) centers said laboratory vessel (12) relative to said axis (A) of said first conveying unit (32);
    said centering device (32, 34, 38, 40, 41, 34) comprises said first conveying unit (32), said horizontally aligned support plate (34), a rotational drive (38) for driving and rotating said first conveying unit (32) and said horizontally aligned support plate (34), a recess (40), and, said recess includes a lateral ring guide (41) for said laboratory vessel (12) which tapers conically in one direction;
    said laboratory vessel (12), said first conveying unit (32), and said horizontally aligned support (34) are rotatable about said axis (A); and,
    said horizontally aligned support (34) and said laboratory vessel (12) are moved in the direction of said conical taper of said lateral ring guide while being rotated, said laboratory vessel (12) is guided by said lateral ring guide (41), and said laboratory vessel is thus centered on said lateral ring guide (41) without any tilting of said laboratory vessel.

2. Conveying device according to claim 1 further comprising:
    a third conveying unit (14, 22) is provided which horizontally conveys a laboratory vessel (12) from an input region (20) to said initial region (30).

3. Conveying device according to claim 2 further comprising:
    a fourth conveying unit (14, 72) is provided which horizontally conveys a laboratory vessel (12) from said initial region (30) to an output region (70).

4. Conveying device according to claim 1 further comprising:
    said support (34) is moved up and down along said vertically aligned axis (A).

5. Conveying device according to claim 1, further comprising:
    said rotational drive (38) is an integral component of said first conveying unit (32).

6. Conveying device according to claim 1, further comprising:
    said centering device has a vertical axis and said vertical axis (A) of said first conveying device (32) are identical.

7. Conveying device according to claim 1, further comprising:
    a position sensor (24) is connected upstream of said initial region (30), said sensor detects the orientation of said laboratory vessel (32) with respect to top and bottom.

8. Conveying device according to claim 7, further comprising:

said position sensor (24) is mounted in the conveying path of said third conveying device (14, 22).

9. Conveying device according to claim 8, further comprising:

said position sensor comprises two light barriers (24a, 24b), said two light barriers are provided which are aligned transversely relative to the conveying direction, F, of said third conveying unit (14, 22);

said light barriers are each assigned to an outer diameter of said laboratory vessel (12) so that the light barrier (24a, 24b) at which the larger outer diameter of said laboratory vessel (12) enters first, will be the first to generate a signal, and then, with some time delay, the other light barrier at which the smaller outer diameter of said laboratory vessel (12) enters, will generate a signal, thus allowing the determination of the orientation of said laboratory vessel (12).

10. Conveying device according to claim 1, further comprising:

said laboratory vessel (12) is of a rotationally symmetrical design and has different diameters along its height; and, said laboratory vessel (12) has a container (12a) which is in particular open to the top and has a first outer diameter and a lid (12b) closing said container (12a) which has a second outer diameter, and, said second outer diameter of said lid (12b) being larger than said first outer diameter of said container (12a).

11. Conveying device according to claim 1, further comprising:

said gripper (56) is rotatably mounted and driven (55) in said support arm (54), thus allowing it to rotate by 180°, and horizontally move the gripped part (12a) of said laboratory vessel (12) in a certain orientation relative to an analysis device (64).

12. Conveying device according to claim 1, further comprising:

a suction device (62) resides between said height region (50) and said provision region (60).

13. Conveying device according to claim 1, further comprising:

a sensor (42) detects when said laboratory vessel (12) that has been vertically moved by said first conveying device (32) has reached a certain height (H).

14. Conveying device (10) for positioning and providing laboratory vessels (12; 12a; 12b; 12c) for nutrient media, samples, microorganisms, cell cultures, for analysis, sample preparation, and/or sample manipulation on an associated apparatus (64), comprising:

said conveying device includes a conveying direction F for said laboratory vessels;

a first conveying unit (32) vertically and translationally conveys said laboratory vessel (12) from said initial region (30) to a predetermined height region (50) along a vertical axis (A) and vice versa;

said first conveying unit (32) comprises a horizontally aligned support plate (34) for said laboratory vessel (12), said horizontally aligned support plate (34) includes a horizontally aligned support surface;

said vertical axis (A) of said first conveying unit (32) extends orthogonally relative to said horizontally aligned support surface of said horizontally aligned support plate (34);

a second conveying unit (52, 56, 54) comprises a support arm (54), said support arm (54) includes a longitudinal axis and a gripper (56) at a free end of said support arm;

a drive (55) translationally moves said support arm (54) and said gripper (56) forward and backward in a horizontal plane orthogonally relative to said conveying direction F and said axis (A;

a drive (58) rotates said gripper (56) about said longitudinal axis of said support arm;

said gripper of said second conveying unit (52) engages said laboratory vessel (12) and translationally and rotationally conveys said laboratory vessel (12) from said vertical axis (A) in said predetermined height region (50) to said provision region in said horizontal plane and vice versa;

said laboratory vessel (12) is held in said provision region for analysis or preparation before it is returned to said predetermined height region (50) along said vertical axis (A);

a centering device (32, 40, 41) centers said laboratory vessel (12) relative to said axis (A) of said first conveying unit (32);

said centering device (32, 34, 38, 40, 41, 34) comprises said first conveying unit (32), said horizontally aligned support plate (34), a rotational drive (38) for driving and rotating said first conveying unit (32) and said horizontally aligned support plate (34), a recess (40), and, said recess includes a lateral ring guide (41) for said laboratory vessel (12) which tapers conically in one direction;

said laboratory vessel (12), said first conveying unit (32), and said horizontally aligned support (34) are rotatable about said axis (A); and, said horizontally aligned support (34) and said laboratory vessel (12) are moved in the direction of said conical taper of said lateral ring guide while being rotated, said laboratory vessel (12) is guided by said lateral ring guide (41), and said laboratory vessel is thus centered on said lateral ring guide (41) without any tilting of said laboratory vessel.

* * * * *